United States Patent [19]

Larsen

[11] Plant 4,009

[45] Jan. 11, 1977

[54] LADY UARDA

[76] Inventor: Carl A. Larsen, 2561 Elm Ave., Salt Lake City, Utah 84109

[21] Appl. No.: 595,070

[22] Filed: July 11, 1975

[51] Int. Cl.[2] ..... A01H 5/00

[52] U.S. Cl. ..... Plants/66

[58] Field of Search ..... Plt./66

[56] References Cited

U.S. PATENT DOCUMENTS 3,695 3/1975 Slater ..... Plt./66

*Primary Examiner*—Robert E. Bagwill

[57] ABSTRACT

A new and distinct variety of *Syringa vulgaris* hybrid French Lilac plant, characterized in that the mature plant is about 9 feet high and about 6 feet wide; and in that its flowers are magenta to burgundy, and very large when compared with other French Lilac hybrid plants, with large florets and tight flowers spikes that are well formed.

2 Drawing Figures

1

This invention relates to a new and distinct variety of lilac plant and particularly to a hybrid French Lilac.

This new variety comes as a result of an extensive selection and planting program, since a great many seedlings have appeared each year in my garden for the past 30 years. I started with 35 distinct named varieties of French Lilacs. Only in the one area have seedlings come up consistently each year and only the most vigorous and healthiest seedling plants were transplanted and left to grow until they bloomed. The new variety has been propagated by layering.

The present variety is distinguished from other French Lilac plants in that it has a clear magenta flower of the colour such as those found in the well known cultivar "Souvenier de Madam Gaudichaud", but the florets and flowers are much larger. The new variety of *Syringa vulgaris* according to the present invention is distinguished from other French Lilac hybrids by its more vertical than horizontal growth habit and very large magenta to burgundy florets and flowers. The flowers of this new variety are formed in from one to three spikes in a group, but the most common seems to be two spikes to a flower stem and very well formed.

The new variety first flowered the first week of June, 1965, and remained in bloom for three weeks before the flowers began fading.

More detailed description of the new variety follows, taken together with the accompanied drawings, of which:

FIG. 1 is a colour photograph, showing as best possible by this method of illustration the shape and colour of the flower spikes of the matured plant according to this invention; and FIG. 2 is a colour photograph illustrating the growth habit of the present variety.

2

THE PLANT

Type: French Lilac *Syringa vulgaris* "LADY UARDA."

Breeding: Hybrid.

Parentage: *Syringa vulgaris* of unknown parentage.

Growth habit: More vertical than horizontal. Growth can be controlled by pruning. The original plant is now 6 feet wide and 9 feet high in 10 years. The branches are stocky, coloured brown as is usual in French Lilac hybrid plants such as the variety "Souv. de Mme. Gaudichaud." No lenticels.

Foliage: Numerous leaves, green, heart shaped, about three or four inches long and 2¾ to 3¼ inches wide: medium thickness; smooth edges; medium petiole.

Flower buds: Hardy; panicle-shaped; dark burgundy colour; darker than the variety "Souv. de Mme. Gaudichaud." The panicle is about 7 or 8 inches long and varies in width with the number of spikes. A single spike flower would be 3 to 3½ across.

Flowers: Abundant flowers, first blooming about the 25th day of May in the Salt Lake region with full bloom on the 5th day of June to the 15th for this new variety. The flowers are large with tight spikes that are well formed. The color is magenta to burgundy, of substantially the same colour as the well known variety "Souv. de Mme. Gaudichaud" but larger. In each floret there are four petals, incurved slightly, each about 1 inch across.

Fruit: Not abundant.

Fragrance: Average.

I claim:

1. A new and distinct variety of *Syringa vulgaris* hybrid French Lilac plant, characterized in that the mature plant is about 9 feet high and about 6 feet wide; and in that its flowers are magenta to burgundy, and very large when compared with other French Lilac hybrid plants, with large florets and tight flowers spikes that are well formed.

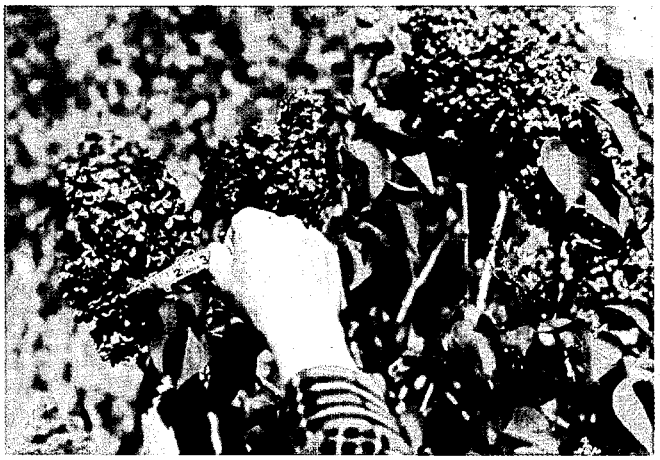
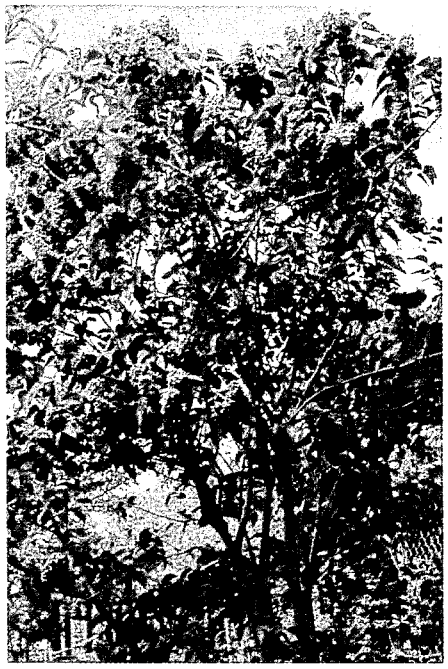

* * * * *